United States Patent [19]

Cavallini

[11] Patent Number: 5,336,678
[45] Date of Patent: Aug. 9, 1994

[54] USE OF MINOXIDIL FOR TREATING ERECTILE IMPOTENCE

[76] Inventor: Giorgio Cavallini, Via Montebello 49, Ferrara, Italy

[21] Appl. No.: 938,060
[22] PCT Filed: Apr. 15, 1991
[86] PCT No.: PCT/EP91/00711
§ 371 Date: Oct. 16, 1992
§ 102(e) Date: Oct. 16, 1992
[87] PCT Pub. No.: WO91/16052
PCT Pub. Date: Oct. 31, 1991

[30] Foreign Application Priority Data

Apr. 19, 1990 [IT] Italy .................................. 9007 A/90

[51] Int. Cl.⁵ .......................................... A61K 31/505
[52] U.S. Cl. .................................................... 514/275
[58] Field of Search .......................................... 514/275

[56] References Cited

U.S. PATENT DOCUMENTS 4,596,812 6/1986 Chidsey et al. ...................... 514/256
4,801,587 1/1989 Voss et al. .......................... 514/248

OTHER PUBLICATIONS

British Journal of Uroiogy, 1988, 62(J) p. 466 (Watters et al.) "Effect on Pharmacological Agents of Erectile Responses in the Dog".

Primary Examiner—Marianne M. Cintins
Assistant Examiner—William R. A. Jarvis
Attorney, Agent, or Firm—Griffin Butler Whisenhunt & Kurtossy

[57] ABSTRACT

A method of treatment of human erectile impotency by topical administration to the penis of a topical composition containing 0.1 to 10% minoxidil.

2 Claims, No Drawings

USE OF MINOXIDIL FOR TREATING ERECTILE IMPOTENCE

The present invention concerns the use of minoxidil for the preparation of a medicament useful for the treatment of erectile impotence.

The treatment of most erectile impotences presently relies on the injection in corpora cavernosa of drugs which, directly acting on the arterial smooth muscles and on cavernous muscles, cause the relaxation thereof, allowing and/or making the hematic repletion and therefore erection, easier.

The drug-induced erection by means of intracavernous injection allow (in cases selected by the papaverine test) a normal sexual intercourse immediately after the injection whereas the normal erections are improved by periodical injections.

Papaverine by the intracavernous route has therefore found wide clinical applications, with a substantial improvement in the therapy of erectile impotence.

Several clinical and experimental research efforts have been paid to the search of new drugs having the same effectiveness of papaverine but lower risks and drawbacks.

It has been recently shown that the erection first induced by the relaxation of corpora cavernosa muscle tissue and of the penis arterial system (Ann. Urol. 19, 327, 1985 e 22, 49, 1988). Myorelaxant or alpha-blocker drugs are therefore potentially useful as erection inducers (Lancet 2,938, 1982; Br. J. Psychometr. 143, 332, 1983; Br. J. Psych. 149, 210, 1986).

The drugs up-to-now studied belong to three different classes, according to the administration route:
1) orally active drugs: yohimbine
2) drugs active by intracavernous injection: papaverine, phentolamine, $PGE_1$ etc.
3) Topical drugs: nitroglycerine.

The drugs for local use (intracavernous and topical) share, as a mechanism of action, the relaxing of smooth muscle fibers and of the arterio-arteriolar system of the penis, causing therefore the first and fundamental event of the erection, as shown by recent studies on the physiology of the erection.

However, none of the presently available drugs is completely satisfactory: for instance, yohimbine is not active against organic impotence whereas the intracavernous administration of drugs such as papaverine, phentolamine, $PGE_1$ has a low compliance because of pain and psychological problems, sometimes even impairing the drug-induced erection. This route involves also substantial risks of priapism and sclerosis of corpora cavernosa after long-term treatment. Finally, topically applied nitroglycerine has been found to induce cephalalgia, hypotension and burning on the application site, typical side-effects of organic nitrates.

It has now been found that topically applied minoxidil is able to make erection easier, side-effects and problems connected with the use of the previously known drugs.

Minoxidil is a vasodilator agent mainly acting on the arterial wall. Its use as antihypertensive is well-established and, more recently, topical applications of minoxidil have been found to be useful for the treatment of androgenetic alopecia Minoxidil, when topically applied, is poorly absorbed from healthy cutis, an average of only 1.4% (range: 0.3–4.5%) of the administered dose being found in the systemic circulation. Thus, the application of 1 ml of 2% Minoxidil solution, corresponding to 20 mg of drug, gives absorption of 0.28 mg (Rep. Farm. H., 1990), very far from the recommended maximum daily antihypertensive dose (100 mg).

A double-blind controlled study has been carried out on 42 patients effected by impotence of different origin, diagnosed by a complete clinical, psychological and instrumental evaluation. The patients affected by uncontrolled diabetes, prepuce sclerosis, La Peyronie disease, recent myocardial infarction, orthostatic hypotension or treated with organic nitrates and minoxidil in the 4 months before the study were not tested.

The etiology is shown in Table 1.

Each patient was given on 3 different days: 2.5 g of 2% nitrogylcerine ointment (Nitrocor®); 1 ml of 2% minoxidil; 2.5 g of urethral lubrificant as placebo (K-J®).

The patients were randomized in three groups of 14, each receiving both nitroglycerine and minoxidil and placebo.

TABLE 1

| Etiology of impotence in 42 examined cases | |
|---|---|
| NEUROGENIC IMPOTENCE | tct. 10 |
| pelvis fracture | 2 |
| pelvis surgery | 4 |
| diabetic neuropathy | 2 |
| spinal trauma | 1 |
| multiple sclerosis | 1 |
| MIXED IMPOTENCE: | tct. 4 |
| arterial + neurogenic (from diabetes) | |
| ARTERIAL IMPOTENCE | tct. 19 |
| diabetic microangiopathy | 6 |
| atherosclerosis | 9 |
| hypertension | 4 |
| PSYCHIC IMPOTENCE | tct. 9 |

Each substance was administered with 4–7 days interval between each other, in three different days so that each group received the drugs in different sequence one from the other (Table 3). The erectile response was evaluated both as increase of the circumference at the penis base (in mm) beyond the basal value and as stiffness at the base (as percent increase above the basal value). Circumference and stiffness were measured by Rigiscan.

TABLE 2

| Distribution design of groups patients | | | |
|---|---|---|---|
| | 1st day | 2nd day | 3rd day |
| group 1 | placebo | nitroglycerine | minoxidil |
| group 2 | nitroglycerine | minoxidil | placebo |
| group 3 | minoxidil | placebo | nitroglycerine |

As a further parameter, the arterial flow in the presence of the compounds under exam was evaluated by Doppler.

The results were statistically analyzed by the randomized blocks variance analysis (1 patient = 1 block) for the main comparisons whereas the individual comparisons were analyzed by orthogonal comparison. The analysis was carried out on natural data (penis circumference) and subjected to angular transformation $sen^{-1}\sqrt{p/100}$.

RESULTS

From the results reported in the following Table 3 and 4 it is evident that minoxidil turned out to be more active, in a statistically significant way, than nitroglycerine and placebo.

Minoxidil turned also out to be practically free from side-effects (only 2 cases of slight burning on the application site) whereas nitroglycerine induced burning in 14 cases, pulsing cephalalgia in 21 cases and hypotension in 4.

TABLE 3

Increase of penis circumference in mm after topical application of minoxidil, nitroglycerine, placebo

|  | Minoxidil | Nitroglycerine | Placebo |
|---|---|---|---|
| Circumference increase in mm.: Mean ± S.D. | 18.6 ± 7.4 | 10.3 ± 4.6 | 5.0 ± 3.8 |
| Variance source | Squares sums | Degree of freedom | Mean squares | F |
| Treatments | 3983.3 | 2 | 1991.6 | 163.7** |
| Patients | 2216.1 | 41 | 54.0 | 4.4** |
| Error | 1520.6 | 125 | 12.1 | |
| Minoxidil v/s Nitroglycerine | 1450.0 | 1 | 1450.0 | 119.2** |
| Minoxidil v/s Placebo | 3922.5 | 1 | 3922.5 | 322.4** |
| Nitroglycerine v/s Placebo | 602.7 | 1 | 602.7 | 49.5** |

** = $p < 0.01$;
* = $p < 0.05$;
§ = p not significant

TABLE 4

Per cent increase of penis stiffness after topical application of minoxidil, nitroglycerine, placebo

|  | Minoxidil | Nitroglycerine | Placebo |
|---|---|---|---|
| % stiffness increase range: min-mx | 0–85 | 0–80 | 0–30 |
| Mean ± S.D. values subjected to angular transformations $sen^{-1}$ p/100 | 42.1 ± 12.8 | 29.4 ± 10.2 | 17.1 ± 10.5 |
| Variance source | Squares sums | Degree of freedom | Mean squares | F |
| Treatments | 7349.0 | 2 | 3674.5 | 55.9** |
| Patients | 13158.8 | 41 | 320.9 | 4.9** |
| Error | 8215.0 | 125 | 65.7 | |
| Minoxidil v/s Nitroglycerine | 34196.6 | 1 | 34196.6 | 520.0** |
| Minoxidil v/s Placebo | 13156.2 | 1 | 13156.2 | 200.2** |
| Nitroglycerine v/s Placebo | 3161.5 | 1 | 3161.5 | 48.1** |

** = $p < 0.01$;
* = $p < 0.05$;
§ = p not significant

These data were confirmed by the Doppler test of the penis artaria: the highest flow was noticed after 2% minoxidil, a lower one after nitroglycerine and still lower after placebo.

From the data reported above, it is evident that minoxidil can be successfully used for the preparation of topical medicaments useful for the treatment of erectile impotence. Said medicaments are prepared by conventional methods for the preparation of topical administration forms, such as described, for instance, in Remington's Pharmaceutical Sciences, Mack Pub. Co., USA. Suitable administration forms include ointments, creams, solutions, sprays, powders, foams, liposome formulations and the like. The compositions of the invention can also be used to coat the inside surfaces of condoms.

Minoxidil may be present in said medicaments in percentages ranging from 0.1 to 10% preferably from 1 to 5% and more preferably from 15 to 2 5%, 2% being particularly preferred. The compositions can also contain other active principles able to induce or facilitate the erection, such as moxisylyte, phentolamine, vasoactive intestinal peptide, papaverine, prostaglandine $E_1$.

A medicament containing 2% of minoxidil and 2% nitrogycerine can be, for instance, successfully used in very difficult and serious cases.

The medicaments of the invention will be applied to induce erection, usually before sexual intercourse, on the glans. This will generally be sufficient to induce or facilitate erection, possibly after the erotic stimulation.

I claim:

1. A method of treating erectile impotence in humans comprising the topical administration on the penis of topical formulations containing from 0.1 to 10% of minoxidil.

2. A method according to claim 1 wherein the topical formulations contain about 2% of minoxidil.

* * * * *